United States Patent [19]
Christensen, IV et al.

[11] Patent Number: 5,710,180
[45] Date of Patent: Jan. 20, 1998

[54] PHENETHYLAMINE COMPOUNDS

[75] Inventors: Siegfried Christensen, IV, Philadelphia; Cornelia Jutta Forster, Bensalem, both of Pa.

[73] Assignee: SmithKline Beecham Corporation, Philadelphia, Pa.

[21] Appl. No.: 596,197

[22] PCT Filed: Aug. 19, 1994

[86] PCT No.: PCT/US94/09308

§ 371 Date: Feb. 16, 1996

§ 102(e) Date: Feb. 16, 1996

[87] PCT Pub. No.: WO95/05386

PCT Pub. Date: Feb. 23, 1995

[51] Int. Cl.$^6$ .......................... A61K 31/16; C07C 233/18
[52] U.S. Cl. .................................. 514/630; 564/219
[58] Field of Search .......................... 564/219; 514/630

[56] References Cited

U.S. PATENT DOCUMENTS 5,066,658 11/1991 Demers et al. .
5,130,472 7/1992 Buzzetti et al. ..................... 564/219

Primary Examiner—Robert W. Ramsuer
Attorney, Agent, or Firm—James M. Kanagy; Stephen Venetianer; Edward T. Lentz

[57] ABSTRACT

Substituted phenethylamines of formula (I) useful for treating phosphodiesterase IV related

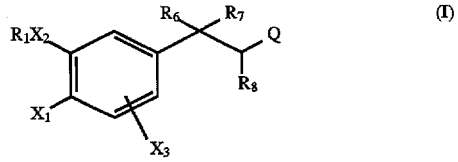

(I)

disease states are disclosed herein.

3 Claims, No Drawings

PHENETHYLAMINE COMPOUNDS

This application is a 371 of PCT/US94/09308 filed Aug. 19, 1994.

FIELD OF THE INVENTION

This invention relates to certain phenethylamines which are useful for treating diseases where antagonizing the enzyme phosphodiesterase IV will have a salutary effect.

BACKGROUND OF THE INVENTION

Bronchial asthma is a complex, multifactorial disease characterized by reversible narrowing of the airway and hyper-reactivity of the respiratory tract to external stimuli.

It is now understood that the symptoms of chronic asthma are the manifestations of three distinct processes: 1) an early response to antigen, 2) a delayed or late response to antigen, and 3) chronic inflammation and airway hyper-reactivity. Cockcroft, Ann. Allergy 55:857–862, 1985; Larsen, Hosp. Practice 22:113–127, 1987. The agents currently available (β-adrenoceptor agonists, steroids, methylxanthines, disodium cromoglycate) are inadequate to control the disease; none of them modify all three phases of asthma and nearly all are saddled with limiting side effects. Most importantly, none of the agents, with the possible exception of steroids, alter the course of progression of chronic asthma.

Identification of novel therapeutic agents for asthma is made difficult by the fact that multiple mediators are responsible for the development of disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit PDE should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cyclic AMP breakdown in airway smooth muscle and inflammatory cells. Torphy, "Phosphodiesterase Isozymes: Potential Targets for Novel Anti-asthmatic Agents" in New Drugs for Asthma, Barnes, ed. IBC Technical Services Ltd. (1989). Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit production of Tumor Necrosis Factor (TNF), a serum glycoprotein. Excessive or unregulated TNF production is implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sacroidosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

TNF has been implicated in various roles with the human acquired immune deficiency syndrome (AIDS). AIDS results from the infection of T lymphocytes with Human Immunodeficiency Virus (HIV). It has now been discovered that monokines, specifically TNF, are implicated in the infection of T lymphocytes with HIV by playing a role in maintaining T lymphocyte activation. Furthermore, once an activated T lymphocyte is infected with HIV, the T lymphocyte must continue to be maintained in an activated state to permit HIV gene expression and/or HIV replication. It has also been discovered that monokines, specifically TNF, are implicated in activated T cell-mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopatho-genesis of HIV Infection, Advances in Immunology, Vol. 57, (1989)]. Monokines, such as TNF, have been shown to activate HIV replication in monocytes and/or macrophages [See. Poli, et al., Proc. Natl. Acad. Sci., 87:782–784 (1990)], therefore, inhibition of monokine production or activity aids in limiting HIV progression as stated above for T cells.

It has now been discovered that monokines are implicated in certain disease-associated problems such as cachexia and muscle degeneration. Therefore, interference with monokine activity, such as by inhibition of TNF production, in an HIV-infected individual aids in enhancing the quality of life of HIV-infected patients by reducing the severity of monokine-mediated disease associated problems such as cachexia and muscle degeneration.

TNF is also associated with yeast and fungal infections. Specifically *Candida Albicans* has been shown to induce TNF production in vitro in human monocytes and natural killer cells. [See Riipi et al., Infection and Immunity, Vol. 58, No. 9, p. 2750–54 (1990); and Jafari et al., Journal of Infections Diseases, Vol. 164, p. 389–95 (1991). See also Wasan et al., Antimicrobial Agents and Chemotherapy, Vol. 35, No. 10, p. 2046–48 (1991) and Luke et al., Journal of Infectious Diseases, Vol. 162, p. 211–214 (1990)].

SUMMARY OF THE INVENTION

The discovery of a class of compounds which inhibit the production of TNF will provide a therapeutic approach for the diseases in which excessive, or unregulated TNF production is implicated. That is provided herewith.

In a first aspect, this invention covers a compound of formula I

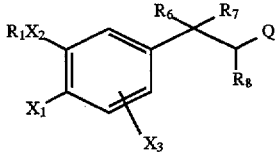

or a salt thereof,
where Q is a radical of formula A, B, C or D

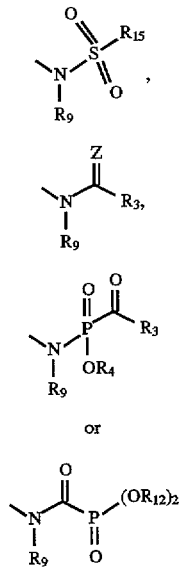

$R_1$ is lower alkyl substituted by 1 or more halogens, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuryl, furyl, tetrahydropyranyl, pyranyl, tetrahydrothienyl, thienyl, tetrahydrothiopyranyl, thiopyranyl, —$CR_4R_5$-$C_{3-6}$ cycloalkyl, $C_{3-6}$ cycloalkyl, or a $C_{4-6}$ cycloalkenyl containing one or two unsaturated bonds, wherein the cycloalkyl and heterocyclyl moieties unsubstituted or substituted by 1 to 3 methyl groups or one ethyl group;

$R_2$ is —$CH_3$ or —$CH_2CH_3$ unsubstituted or substituted by 1 or more halogens;

$R_3$ is lower alkyl unsubstituted or substituted by one or more halogens, —$CR_4R_5OR_4$, —$CR_4R_5NR_4R_9$, —$CR_4$ ($OR_4$)$CR_4R_5OR_4$, 2,2-dimethyl-1,3-dioxolan-4-yl, —$NR_9C$(O)$NR_4R_9$, —$NR_4R_9$, —$S(CR_4R_5)_nCH_3$ where n is 0-5, or —$P(O)(OR_{12})_2$;

$R_4$ and $R_5$ are independently hydrogen, methyl or ethyl;

$R_6$ is hydrogen, halogen, —$C_{1-4}$ alkyl, halo-substituted $C_{1-4}$ alkyl, —$CH_2NHC(O)C(O)NH_2$, —$CH$—$CR_4R_5$, cyclopropyl unsubstituted or substituted by $R_4$, —CN, —$OR_4$, —$CH_2OR_4$, —$NR_4R_5$, —$CH_2NR_4R_5$, —$C(O)R_4$, —$C(O)OR_4$, —$C(O)NR_4R_5$, or —$C\equiv CR_4$; provided that when $R_6$ is OH, then $R_7$ is hydrogen or —$CH_3$ unsubstituted or substituted by 1 to 3 fluoro groups;

$R_7$ is hydrogen, F, —CN, or —$CH_3$ unsubstituted or substituted by 1 to 3 fluoro groups, or $R_6$ and $R_7$ together can form a keto (=O) moiety;

$R_8$ is H, F, CN, $C_{1-2}$ alkyl optionally substituted by 1 or more fluoro groups, $C(O)NR_4R_5$, or $C(O)OR_4$;

$R_9$ is H, —$OR_{11}$, unsubstituted or substituted —$(CH_2)_m$Ar where m is 0–2, or unsubstituted or substituted $C_{1-6}$ alkyl, wherein optional substituents comprise from one to three groups independently selected from the group consisting of —$CH_3$ or —$CH_2CH_3$ unsubstituted or substituted by 1 or more halogens, —$NO_2$, —$Si(R_4)_3$, —$NR_{10}R_{11}$, —$C(O)R_4$, —$C(O)OR_4$, —$OR_4$, —CN, —$C(O)NR_{10}R_{11}$, —$OC(O)NR_{10}R_{11}$, —$OC(O)R_{12}$, —$NR_{10}C(O)NR_{10}R_{11}$, —$NR_{10}C(O)R_{11}$, —$NR_{10}C(O)OR_{12}$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_{12}$, —$S(O)_{m'}R_{12}$ where m' is 0–2, —$NR_{10}C(O)C(O)NR_{10}R_{11}$, —$NR_{10}C(O)C(O)R_{10}$, thiazolyl, imidazolyl, oxazolyl, pyrazolyl, triazolyl, and tetrazolyl;

$R_{10}$ is —$OR_{11}$ or —$R_{11}$;

$R_{11}$ is hydrogen, or —$C_{1-4}$ alkyl unsubstituted or substituted by one to three fluoro groups; or when $R_{10}$ and $R_{11}$ are comprise part of the group —$NR_{10}R_{11}$ they may together with the nitrogen form a 5 to 7 membered ring which may contain at least one additional heteroatom which is O, N, or S;

$R_{12}$ is —$C_{1-4}$ alkyl unsubstituted or substituted by one to three fluoro groups;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, wherein each of these heterocyclic rings is connected through a carbon atom and each may be unsubstituted or substituted by one or two $C_{1-2}$ alkyl groups;

$R_{14}$ is OH or $OR_{12}$;

$R_{15}$ is unsubstituted or substituted —$(CH_2)_m$Ar where m is 0–2, or unsubstituted or substituted $C_{1-6}$ alkyl, wherein optional substituents comprise from one to three groups independently selected from the group consisting of —$CH_3$ or —$CH_2CH_3$ unsubstituted or substituted by 1 or more halogens, —$NO_2$, —$Si(R_4)_3$, —$NR_{10}R_{11}$, —$C(O)R_4$, —$C(O)OR_4$, —$OR_4$, —CN, —$C(O)NR_{10}R_{11}$, —$OC(O)NR_{10}R_{11}$, —$OC(O)R_{12}$, —$NR_{10}C(O)NR_{10}R_{11}$, —$NR_{10}C(O)R_{11}$, —$NR_{10}C(O)OR_{12}$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_{12}$, —$S(O)_{m'}R_{12}$ where m' is 0–2, —$NR_{10}C(O)C(O)NR_{10}R_{11}$, —$NR_{10}C(O)C(O)R_{10}$, thiazolyl, imidazolyl, oxazolyl, pyrazolyl, triazolyl, and tetrazolyl;

Ar is 2-, 3- or 4-pyridyl, pyrimidyl, pyridazyl, 2-imidazolyl, morpholino, or phenyl;

$X_1$ is $YR_2$, halogen, nitro, —$NR_4R_5$, or formyl amine;

$X_2$ is O or $NR_4$;

$X_3$ is hydrogen or $X_1$;

Y is O, S, SO or $SO_2$;

Z is O or NCN;

provided that a) Z is NCN only when $R_3$ is —$NR_4R_5$ or —$S(CR_4R_5)_nCH_3$; or b) when $X_1$ is —$NR_4R_5$ or formyl amine, then $R_1$ is not $CH_3$ or $C_2H_5$ when $X_2$ is O and $X_3$ is H or halogen; or c) when $R_3$ is $CR_4R_5NR_4R_9$, and $X_2$ is O, and $R_1$ is phenyl, then one of $R_6$, $R_7$, or $R_8$ is other than H; or d) when Z is NCN, and $X_1$ is $YR_2$, and Y is O, and $R_2$ is $CH_3$ and $R_3$ is $NH_2$, and $R_9$ is H, OH, $OCH_3$ or $CH_3$, and $R_8$ is H and $R_6$ and $R_7$ are both hydrogen, or are hydrogen and methyl, hydrogen and $CF_3$ or hydrogen and ethyl, and $X_2$ is O, then $R_1$ is not $CF_3$, $CF_2H$, or $CF_2CF_2H$; or e) when Z is NCN, and X is $YR_2$, and Y is O, and $R_2$ is $CH_3$ and $R_3$ is $NH_2$, and $R_9$ is H, OH $OCH_3$ or $CH_3$, and $R_8$ is H, and $R_6$ and $R_7$ are both hydrogen, or are hydrogen and methyl, hydrogen and $CF_3$ or hydrogen and ethyl, and $X_2$ is $NR_4$ and $R_4$ is $CH_3$, then $R_1$ is not $CH_3$; or f) when Q is A, and $X_2$ is O, $R_1$ is aryl or halo-substituted aryl, $R_6$ is halo or $OR_4$, $R_7$ is H, $R_8$ is $CH_3$ or $CH_2F$ and $R_9$ is H or $C_{1-3}$alkyl, then $R_{15}$ is not lower alkyl, mono or dichlorosubstituted lower alkyl, or unsubstituted or subsitituted phenyl; or g) when Q is B, and $X_2$ is O, $R_1$ is aryl or halo-substituted aryl, $R_7$ is H, $R_8$ is $CH_3$ or $CH_2F$; $R_9$ is H or $C_{1-3}$alkyl, then $R_6$ is other than halo or $OR_4$.

These compounds are useful in the mediation or inhibition of the enzymatic activity (or catalytic activity) of phosphodiesterase IV (PDE IV). The novel compounds of the Formula (I) also have Tumor Necrosis Factor (TNF) inhibitory activity.

This invention also relates to a composition, including a pharmaceutical composition, comprising a compound of the Formula I and a carrier or diluent.

The invention also relates to a method of mediation or inhibition of the enzymatic activity (or catalytic activity) of phosphodiesterase IV, including mammals which comprises administering to a mammal in need thereof an effective amount of a compound of Formula I.

The invention further provides a method for treating allergic and inflammatory diseases which comprises administering to a mammal, including humans, in need thereof, an effective amount of a compound of the Formula I.

The invention also provides a method for treating asthma which comprises administering to a mammal, including humans, in need thereof an effective amount of a compound of the Formula I.

This invention also relates to a method of inhibiting TNF production in a mammal, including humans, which method comprises administering to a mammal in need of such treatment an effective TNF inhibiting amount of a compound of the Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of the Formula (I).

The compounds of the Formula (I) are also useful in the treatment of additional viral infections, where such viruses are sensitive to upregulation by TNF or will elicit TNF production in vivo.

In yet a further aspect, this invention covers a process for making a compound of formula I, which process comprises one or more of the following steps:

a) forming a salt;

b) treating an amine with a lower alkyl acylating agent to form the corresponding amide;

c) treating an amine with biuret to form the corresponding imidodicarbamide;

d) hydrolyzing the product of an amine treated with trimethylsilyl isocyanate to form the corresponding urea;

e) treating an amine with cyanodithioiminiocarbonate to form the corresponding $N^2$-cyano-S-methyl-$N^1$-isothiouriedo;

f) treating an $N^2$-cyano-S-methyl-$N^1$-isothiouriedo with an amine to form the corresponding N'-cyanocarboximidamide;

g) treating a amine with a mixture comprising (4S)-2,2-dimethyl-1,3-dioxolane-4-carboxylic acid and isobutyl chloroformate in the presence of an organic base to form the corresponding 2,3-dihydroxypropanamide and the corresponding carbamate;

h) treating an amine with 4(R)-2,2-dimethyl-1,3-dioxaolane-4-carboxylic acid to form the corresponding 2,2-dimethyl-1,3-dioxolane-4-carboxamide;

i) treating an amine with trimethyl phosphonoformate to form the corresponding phosphonoformamide;

j) reacting an amine with dimethoxyformylphosphonyl chloride;

k) treating an aminopropionitrile with acetoacetyl chloride to form the corresponding 2-acetoxyacetamide;

l) hydrolyzing a protected aminoacetamide to form the corresponding 2-aminoacetamide; or m) treating an amine with a sulfonylating agent to form the corresponding sulfonamide.

SPECIFIC EMBODIMENTS

Specific embodiments of this invention are defined and illustrated below.

The following terms and phrases used herein are to be interpreted as having the meaning or meanings given hereafter. "Lower alkyl" means a group having 1 to 6 carbon atoms. This included normal, secondary and tertiary form where such forms can exist, e.g., isopropyl, t-butyl and the like. Normal, or linear, radicals are preferred, especially methyl, ethyl, propyl, butyl, pentyl and hexyl. Halo means fluoro, chloro, bromo and iodo. The term "cycloalkyl" or "cycloalkyl alkyl" as used herein is meant to include those rings of 3–7 carbon atoms, such as cyclopropyl, cyclopropylmethyl, cyclopentyl or cyclohexyl. "Aryl", unless specified otherwise, means an aromatic ring or ring system of 6–10 carbon atoms such as phenyl. Preferably the aryl is monocyclic, i.e., phenyl. The alkyl chain is meant to include both straight or branched chain radicals of 1 to 4 carbon atoms.

Some compounds of formula I may be sufficiently basic so as form acid addition salts. This work includes all such salts, particularly those which retain the activity of the parent base and are acceptable for pharmaceutical use. Making acid addition salts is a well know art and any documented procedure is expected to provide the desired product in the context of this invention.

"Inhibiting the production of TNF" means, a) a decrease of excessive in vivo TNF levels in a human to normal levels or below normal levels by inhibition of the in vivo release of TNF by all cells, including but not limited to monocytes or macrophages;

b) a down regulation, at the translational or transcription level, of excessive in vivo TNF levels in a human to normal levels or below normal levels; or c) a down regulation, by inhibition of the direct synthesis TNF as a postrunslational event.

"TNF mediated disease states" means all disease states in which TNF plays a role, either by production of TNF itself, or by TNF causing another cytokine to be released, such as but not limited to IL-1, or IL-6. A disease state in which IL-1, for instance is a major component, and whose production or action is exacerbated or which is secreted in response to TNF, would therefore be considered a disease state mediated by TNF.

"Cytokine" means any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines for the present invention include, but are not limited to Interleukin-1 (IL-1), Interleukin-6 (IL-6), Tumor Necrosis Factor-alpha (TNF-α) and Tumor Necrosis Factor beta (TNFβ). Some compounds of formula I may exist in two distinct enantiomeric forms. Some compounds of Formula I may exist in at least two distinct diasteriomeric forms possessing distinct physical and biological properties. Furthermore some compounds of Formula I may exist in a tautomeric form, such as the enol or enamine. All these forms are within the scope of this invention.

Preferred $R_1$ groups are cyclopropylmethyl, cyclopentymethyl, cyclohexylmethyl, cyclobutyl, cyclopentyl, cyclohexyl, tetrahydrofur-2-yl, cyclopentenyl, benzyl, or lower alkyl optionally substituted by 1 or more fluoro groups. When $R_1$ is lower alkyl substituted by 1 or more halogens, the halogens are preferably fluorine and chlorine, more preferably a $C_{1-4}$ alkyl substituted by 1 or more fluoro groups, more preferably 1 or more times by fluorine. The most preferred halo substituted chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents are cyclopentyl, cyclopropylmethyl, —$CF_3$, and —$CHF_2$.

When $R_1$ is a $C_{7-11}$ polycycloalkyl, examples are bicyclo[2.2.1]-heptyl, bicyclo[2.2.2]octyl, bicyclo[3.2.1]octyl, tricyclo 5.2.1.0$^{2,6}$]decyl, additional examples of which are described in Saccamano et al., WO 87/06576, published 5 Nov. 1987 which is incorporated herein by reference in its entirety.

Oxygen is the preferred $X_2$ radical.

As for $X_1$, the preferred radical is $YR_2$ where Y is oxygen. The preferred $R_2$ group is a methyl or ethyl unsubstituted or substituted by 1 or more halogens. The preferred halogens are fluoro and chloro, most preferably fluoro. The more preferred $R_2$ groups are methyl, —$CF_3$, —$CHF_2$, or —$CH_2CHF_2$ moiety. Most preferred are difluoromethyl and methyl.

Hydrogen is the referred $X_3$ radical.

As regards the Q group, the preferred radicals are those which form an amide, sulfonamide, imidodicarbamide, urea, $N^2$-cyano-S-methyl-$N^1$-isothiouriedo, 2,3-dihydroxypropanamide, 2,2-dimethyl-1,3-dioxolane-4-carboxamide, 2-acetoxyacetamide, or a 2-aminoacetamide.

Preferred $R_6$ moieties are H, C(O)NH$_2$, C≡CR$_4$, CN, C(O)H, CH$_2$OH, CH$_2$F, CF$_2$H, and CF$_3$. More preferred are C≡CH and CN. $R_7$ is preferably H or CN. $R_8$ is preferably H, —C(O)NH$_2$ or CN.

Preferred $R_9$ moieties include hydrogen, optionally substituted —(CH$_2$)$_{0-2}$(2-, 3- or 4-pyridyl), (CH$_2$)$_{1-2}$(2-imidazolyl), (CH$_2$)$_2$(4-morpholinyl), (CH$_2$)$_2$(4-piperazinyl), (CH$_2$)$_{1-2}$(2-thienyl), (CH$_2$)$_{1-2}$(4-thiazolyl), and (CH$_2$)$_{0-2}$phenyl.

Preferred rings when $R_{10}$ and $R_{11}$ in the moiety —$NR_{10}R_{11}$ together with the nitrogen to which they are attached form a 5 to 7 membered ring optionally containing at least one additional heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred $R_{15}$ moieties include, optionally substituted $C_{1-3}$alkyl, —(CH$_2$)$_{0-2}$(2-, 3-or 4-pyridyl), (CH$_2$)$_{1-2}$(2-imidazolyl), (CH$_2$)$_2$(4-morpholinyl), (CH$_2$)$_2$(4-piperazinyl), (CH$_2$)$_{1-2}$(2-thienyl), (CH$_2$)$_{1-2}$(4-thiazolyl), and (CH$_2$)$_{0-2}$phenyl.

Preferred rings for $R_{13}$ include (2-, 4- or 5-imidazolyl), (3-, 4- or 5-pyrazolyl), (4or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

Preferred are those compounds of formula (I) wherein $R_1$ is —CH$_2$-cyclopropyl, —CH$_2$—C$_{5-6}$ cycloalkyl, —C$_{4-6}$ cycloalkyl, tetrahydrofuran-3-yl, (3- or 4-cyclopentenyl), benzyl, and —$C_{1-2}$ alkyl optionally substituted by 1 or more fluorines; $R_2$ is methyl or fluoro-substituted alkyl; $R_6$ is CN or C≡CR$_4$; and X is $YR_2$.

Most preferred are those compounds wherein $R_1$ is —CH$_2$-cyclopropyl, cyclopentyl, or CF$_2$H; $R_6$ is CN or C≡CH; X is $YR_2$; Y is oxygen; $X_2$ is oxygen; $X_3$ is hydrogen; and $R_2$ is CF$_2$H or methyl.

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, inflammatory bowel disease states including Crohn's disease, reperfusion injury of the myocardium and brain, chronic glomerulonephritis, endotoxic shock and adult respiratory distress syndrome. In addition, PDE IV inhibitors are useful in treating diabetes insipidus, (Kidney Int. 37:362, 1990; Kidney Int. 35:494, 1989) and central nervous system disorders such as depression and multi-infarct dementia.

Compounds of Formula I are useful in treating, prophylactically or therapeutically, disease states in humans which are exacerbated or caused by excessive or unregulated TNF production. Therefore, the present invention also provides a method for inhibiting the production of tumor necrosis factor (TNF) in an animal in need thereof, including humans, which method comprises administering to said animal an effective amount of a compound of formula I alone or mixed with a carrier.

Compounds of the Formula I may be administered systemically, topically, parenterally or by inhalation in conventional dosage forms prepared by combining such agent with standard carriers according to conventional procedures in an mount sufficient to produce the desired therapeutic activity for treatment of a TNF-mediated disease state or for use as a PDE IV inhibitor.

The daily dosage regimen, based on oral administration, is suitably about 0.001 mg/kg to 100 mg/kg, preferably 0.01 mg/Kg to 40 mg/Kg, of a compound of the Formula I or a pharmaceutically acceptable salt thereof calculated as the free base. The active ingredient may be administered from 1 to 6 times a day, sufficient to exhibit activity. Other doseage regimens may require more or less compound depending on the route by which they are administered, by the enchancing or retarding affects of excipients, to name two factors which can influence the dosage regimen. But optimizing a dosage regimen is within the scope of a person skilled in the art and can be determined by following well established techniques for determining what may constitute an effective amount to compound in a given situation.

The mount of a compound of the formula I required for therapeutic effect on topical administration will, of course, vary with the compound chosen, the nature and severity of the condition and the animal undergoing treatment, and is ultimately at the discretion of the one directing the use of these compounds.

While it is possible for an active ingredient to be administered alone as the raw chemical, it is preferable to present it via a vehicle of some sort. Appropriate forms for using these compounds may be prepared by conventional techniques. For pharmaceutical or veterinary use, a composition of the present invention will comprising an effective, non-toxic amount of a compound of the formula I and a pharmaceutically acceptable carrier or diluent. The carrier(s) must be 'acceptable' in the sense of being compatible with the other ingredients of the formulation and not deleterious in the intended use. Preferably the composition is in unit dosage form, for example a tablet, capsule or metered aerosol dose, so that the patient may self-administer a single dose.

By systemic administration is meant oral, intravenous, intraperitoneal, topical, inhalation and intramuscular administration. By topical administration is meant non-systemic administration and includes the application of a compound externally to the epidermis, to the buccal cavity and instillation of such a compound into the ear, eye and nose, and where the compound does not significantly enter the blood stream. The term 'parenteral' as used herein includes intravenous, intramuscular, subcutaneous intranasal, intrarectal, intravaginal or intraperitoneal administration. The subcutaneous and intramuscular forms of parenteral administration are generally preferred.

For oral administration each dosage unit may contains from 1 mg to 100 mg, and preferably from 10 mg to 30 mg of a compound of the formula I or a pharmaceutically acceptable salt thereof calculated as the free base. Appropriate dosage forms for inhalation include an aerosol formulation or a metered dose inhaler. The daily dosage regimen for a compound of the Formula (I) for intranasal administration and oral inhalation is suitably about 10 to about 1200 mg. As for topical use, a suitable dose of a TNF production inhibiting compound of the formula I is from about 0.01 mg to about 100 mg of base for topical administration, the most preferred dosage being about 0.01 mg to about 30 mg, for example, 0.003 mg to 10 mg administered two or three times daily. Formulations suitable for topical administration include liquid or semi-liquid preparations suitable for penetration through the skin to the site of inflammation such as liniments, lotions, creams, ointments or pastes, and drops suitable for administration to the eye, ear or nose.

No unacceptable toxicological effects are expected when these compounds are administered in accordance with the present invention.

SYNTHETIC METHODS

Compounds of Formula I can be prepared by one of skill in the art according to the procedures outlined in the Examples, infra. The preparation of any remaining compounds of the Formula I not described therein may be prepared by the analogous processes disclosed herein.

In general an amine is first prepared, that is a compound where R is $NH_2$, and then this intermediate is converted to the desired target compound by one or more steps, all of which are described below. These amines can be prepared by the methods set out in PCT/US91/04795; those processes and the amines disclosed there are incorporated herein by reference to the extent that information is necessary or useful for understanding how to make the amine precursors used in this work. By way of illustration, a benzaldehyde of formula (a)

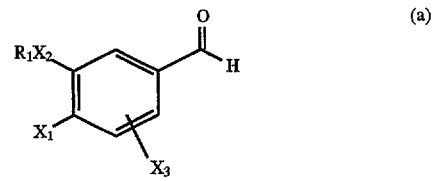

is reacted with nitromethane in a suitable solvent such as acetic acid with a catalyst at between about 80°–100° C. or using the conditions of Shales, et al., *J. Amer. Chem. Soc.*, 74, 4486 (1952) to provide the alkenylnitrate of formula (b).

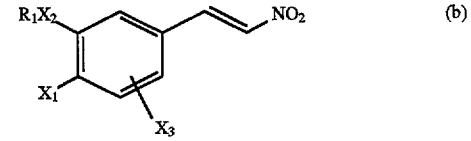

Treating formula b with a reducing agent such as lithium aluminum anhydride or hydrogen with a heavy metal catalyst and an acid yields the corresponding amine.

Alternatively, the aldehyde of formula a can be treated with a lithium halide and a silyl halide in an appropriate solvent followed by a reducing agent, e.g., siloxane, providing a halide of formula (c)

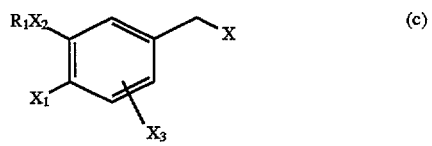

where $X_4$ is the halogen derived from the lithium halide. Cyanide is then used to displace the halide. This nitrile is then reduced, for example by hydrogen and suitable heavy metal catalyst such as nickel with ammonia or palladium on carbon with an acid such as perchloric acid to obtain the primary amine.

Where $R_6$ is nitrile, such compounds can be prepared by dehydrating a compound of formula (d)

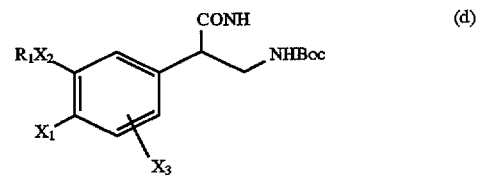

using a reagent such as trifluoroacetic anhydride. This converts the amide to the nitrile and subsequently the Boc group is hydrolized, providing the primary amine. Alternative protecting groups can be used. See for example those disclosed in Greene, I., Protective Groups in Organic Synthesis, Wiley Publishers, NY (USA) (1981). Methods for making this compound are described in PCT/US91/04795, the publication noted above.

Converting the primary amines to compounds of formula I is illustrated in the Examples set out below. These chemistries, and analogous processes, will make all of the compounds of formula I.

ASSAY METHODS

The assay(s) used to confirm the PDE IV antagonistic activity of these compounds can be found in patent application PCT/US91/04795 (International Publication No. WO 92/00968) published 23 Jan. 1992. That information is incorporate herein by reference. The compounds of formula I have exhibited activity at levels consistent with those believed to be useful in treating PDE IV related disease states in those assays.

The following Examples are given to illustrate how to make compounds of formula I and formulations and testing processes for confirming their activity. These are only examples and are not intended to limit the invention in any fashion or with regards to its scope.

EXAMPLES

Example 1

2-(3-Cyclopentyloxy-4-methoxyphenyl)ethylamine 1a. 3-Cyclopentyloxy-4-methoxybenzaldehyde A mixture of 3-hydroxy-4-methoxybenzaldehyde (40 g, 0.26 mol), potassium carbonate (40 g, 0.29 mol) and bromocyelopentane (32 mL, 0.30 mol) in dimethylformamide (0.25 L) was heated under an argon atmosphere at 100° C. After 4 h, additional bromocyclopentane (8 mL, 0.07 mol) was added and heating was continued for 4 h. The mixture was allowed to cool and was filtered. The filtrate was concentrated under reduced pressure and the residue was partitioned between ether and aqueous sodium carbonate. The organic extract was washed with aqueous sodium carbonate and dried (potassium carbonate). The solvent was removed in vacuo and the residue was purified by flash chromatography, eluting with 2:1 hexanes/ether, to provide a pale yellow oil.

Analysis Calc. for $C_{13}H_{16}O_3$: C 70.89, H 7.32; found: C 70.71, H 7.33.

1b. 3-Cyclopentyloxy-4-methoxy-β-nitrostyrene To a solution of 3-cyclopentyloxy-4-methoxybenzaldehyde (6.04 g, 27.4 mmol) in glacial acetic acid (36 mL) under an argon atmosphere was added nitromethane (7.35 mL, 136.0 mmol) and ammonium acetate (3.15 g, 40.9 mmol). The resulting mixture was heated at reflux for 3 h, then allowed to cool to room temperature. The mixture was poured into water and extracted twice with methylene chloride. The combined organic extracts were washed successively with aqueous sodium bicarbonate and water and dried (potassium carbonate). Removal of the solvent in vacuo and purification of the residue by flash chromatography, eluting with 1:1 methylene chloride/hexanes, provided the nitrostyrene as a bright yellow solid: m.p. 133°–134° C.

Analysis Calc. for $C_{14}H_{17}NO_4$: C 63.87, H 6.51, N 5.32; found: C 64.08, H 6.42, N 5.33.

1c. 2-(3-Cyclopentyloxy-4-methoxyphenyl)ethylamine. To a suspension of lithium aluminum hydride (10.8 g, 28.5 mmol) in ether (250 mL) at 0° C. under an argon atmosphere was added dropwise a solution of 3-cyclopentyloxy-4-methoxy-β-nitrostyrene (15 g, 57.0 mmol) in tetrahydrofuran (85 mL). The resulting mixture was allowed to warm to room temperature and stirred overnight. The reaction mixture was cooled to 0° C. and quenched by the successive dropwise addition of water (11 mL), 15% sodium hydroxide (11 mL) and water (33 mL). The mixture was filtered through a pad of Celite and the flu-ate was washed successively with water, 10% hydrochloric acid and water. The aqueous washes were combined, made basic with saturated aqueous potassium carbonate and extracted three times with ether and twice with methylene chloride. The organic layers were combined and dried (potassium carbonate). Removal of the solvent in vacuo provided the amine. A portion of the crude amine was purified by flash chromatography, eluting with 1:10:90 water/methanol/chloroform.

Analysis Calc. for $C_{14}H_{21}NO_2 \cdot 5/8\ H_2O$: C 68.19, H 9.09, N 5.68; found: C 68.39, H 9.16, N 5.85

Example 2

N-[2-(3-Cyclopentyloxy-4-methoxyphenyl)ethyl] acetamide

To a solution of crude 2-(3-cyclopentyloxy-4-methoxyphenyl)ethylamine (0.5 g, 2.1 mmol) in pyridine (1.8 mL) under an argon atmosphere was added acetic anhydride (1.25 mL). The resulting solution was stirred at room temperature for 16 h and then concentrated under reduced pressure. The residue was dissolved in methylene chloride, washed with water and dried (sodium sulfate). The solvent was removed in vacuo, the residue was purified by flash chromatography, eluting with 4% methanol/ether, and then triturated with ether to provide the acetamide: m.p. 87°–88° C.

Analysis Calc. for $C_{16}H_{23}NO_3$: C 69.29, H 8.36, N 5.05; found: C 69.11, H 8.17, N 5.00.

Example 3

N-[2-(3-Cyclopentyloxy-4-methoxyphenyl)ethyl] methanesulfonamide

To a solution of crude 2-(3-cyclopentyloxy-4-methoxyphenyl)ethylamine (0.25 g, 1.1 mmol) in methylene chloride (2 mL) at 0° C. under an argon atmosphere was added triethylamine (0.2 mL, 1.43 mmol) and methanesulfonyl chloride (0.106 mL, 1.37 mmol). The resulting solution was stirred at room temperature for 16 h, diluted with methylene chloride, washed with water and dried (magnesium sulfate). The solvent was removed in vacuo, the residue was purified twice by flash chromatography, eluting with 1:2 hexane/ether, to provide an oil.

MS (DCI, $CH_4$) m/e 313 ($M^+$).

Example 4

Dimethyl N-[2-(3-cyclopentyloxy-4-methoxyphenyl)ethyl]phosphonoformamide

A mixture of trimethyl phosphonoformate (0.27 mL, 2.0 mmol) and 2-(3-cyclopentyloxy-4-methoxyphenyl) ethylamine (0.47 g, 2.0 mmol) was allowed to stand under an argon atmosphere for 3 h. During this time, the mixture was sonicated twice for 3 min. The mixture was dissolved in methylene chloride and washed successively with 10% hydrochloric acid and water and dried (potassium carbonate). The solvent was removed in vacuo and the residue was purified by two successive flash chromatographies, eluting first with 1.5:98.5 methanol/ methylene chloride and subsequently with 75:25 ethyl acetate/hexanes, to provide the phosphonoformamide.

Analysis Calc. for $C_{17}H_{26}NO_6P \cdot 3/4\ H_2O$: C 53.04, H 7.20, N 3.64, P 8.05; found: C 52.94, H 6.92, N 3.61, P 8.15.

Example 5

N-[2-(3-Cyclopentyloxy-3-methoxyphenyl)ethyl] imidodicarbamide

A solution of 2-(3-cyclopentyloxy-4-methoxyphenyl) ethylamine (0.24 g, 1.0 mmol) and biuret (0.52 g, 5.0 mmol) in dimethylformamide (6 mL) under an argon atmosphere was heated to 110° C. for 3 h. The reaction mixture was allowed to cool to room temperature and was concentrated under reduced pressure. The residue was partitioned between methylene chloride and water, and the organic extract was dried (magnesium sulfate). The solvent was removed in vacuo and the residue was purified by flash chromatography, eluting first with 10% ethyl acetate/methylene chloride and then with 4% methanol/methylene chloride. An off-white solid was obtained, which was further purified by flash chromatography, eluting with 2.5% methanol/methylene chloride, to provide an off.

Analysis Calc. for $C_{16}H_{23}N_3O_4 \cdot 1/2$ $H_2O$: C 58.16, H 7.32, N 12.69; found: C 58.34, H 7.12, N 12.72.

Example 6

Dimethyl N-[2-(3-cyclopentyloxy-4-methoxyphenyl)ethylamino]phosphonoformate

To phosphorus pentachloride (0.42 g, 2.0 mmol) was added trimethyl phosphonoformate (0.27 mL, 2.0 mmol) and the resulting mixture was stirred at room temperature under an argon atmosphere for 4 h. The mixture was concentrated under reduced pressure, dissolved in tetrahydrofuran (2 mL) and added to a −78° C. solution containing 2-(3-cyclopentyloxy-4-methoxyphenyl)ethylamine (0.48 g, 2.0 mmol) and diisopropylethylamine (0.39 mL, 2.2 mmol) in tetrahydrofuran (3 mL) under an argon atmosphere. The reaction mixture was stirred for 1.5 h at −78° C. and quenched by the addition of ammonium chloride. The solvent was removed under reduced pressure, and the residue was partitioned between dilute aqueous hydrochloric acid and methylene chloride. The organic extract was washed with water and dried (potassium carbonate). The solvent was removed in vacuo and the residue was purified by two successive flash chromatographies, eluting first with 2.5:50:50 methanol/methylene chloride/hexanes and subsequently with 15:85 ethyl acetate/methylene chloride, to provide the phosphonoformate.

Analysis Calc. for $C_{17}H_{26}NO_6P \cdot 1/3$ $H_2O$: C 54.11, H 7.12, N 3.71, P 8.21; found: C 54.21, H 7.20, N 3.82, P 8.24.

Example 7

N-[2-(3-Cyclopentyloxy-4-methoxyphenyl)ethyl] urea

To a solution of 2-(3-cyclopentyloxy-4-methoxyphenyl) ethylamine (0.47 g, 2.0 mmol) in tetrahydrofuran (10 mL) under an argon atmosphere was added trimethylsilyl isocyanate (0.42 mL, 3.1 mmol). The resulting mixture was heated at reflux for 1 h, was allowed to cool to room temperature and then was stirred overnight. The reaction mixture was again heated to reflux for an additional 5 h and allowed to cool to room temperature. Ammonium chloride was added, and the mixture was concentrated under reduced pressure. The residue was partitioned between methylene chloride and water. The organic extract was washed successively with 10%. hydrochloric acid and water and dried (potassium carbonate). Removal of the solvent in vacuo and purification of the residue by flash chromatography, eluting with 3% methanol/methylene chloride, provided the urea as a white solid: m.p. 136°–37° C. Analysis Calc. for $C_{15}H_{22}N_2O_3$: C 64.73, H 7.97, N 10.06; found: C 64.66, H 7.97, N 10.28.

Example 8

1-($N^2$-Cyano-S-methyl-$N^1$-isothiouriedo)-2-(3-cyclopentyloxy-4-methoxyphenyl)ethane To a solution of 2-(3-cyclopentyloxy-4-methoxyphenyl) ethylamine (0.31 g, 1.31 mmol) in dry pyridine (5 mL) under an argon atmosphere was added dimethyl N-cyanodithioiminiocarbonate (0.37 g, 2.56 mmol). The resulting mixture was heated at reflux for 3 h, then allowed to cool to room temperature and concentrated under reduced pressure. The residue was dissolved in methylene chloride and washed successively with dilute aqueous hydrochloric acid and water and dried (potassium carbonate). The solvent was removed in vacuo and the residue was purified by flash chromatography, eluting with 4:6 ethyl acetate/hexanes, to provide a white solid: m.p. 112°–113° C.

Analysis Calc. for $C_{17}H_{23}N_3O_2S \cdot 1/3$ $H_2O$: C 60.15, H 7.03, N 12.38, S 9.44; found: C 60.02, H 6.93, N 12.55, S 9.26.

Example 9

N'-Cyano-1-[2-(3-cyclopentyloxy-4-methoxyphenyl) ethyl]carboximidamide

A solution of 1-($N_2$-cyano-S-methyl-$N^1$-isothiouriedo-2-(3-cyclopentyloxy-4-methoxyphenyl)ethane (0.22 g, 0.67 mmol) in tetrahydrofuran (4 mL) was added to a suspension of sodium hydride (80% dispersion, 0.027 g, 0.9 mmol) in tetrahydrofuran (2.5 mL) at room temperature under an argon atmosphere. After 2 h, the mixture was heated to 50° C. for 2 h, was cooled to room temperature, was treated with di-t-butyldicarbonate (0.29 g, 1.34 mmol) and was allowed to stir at room temperature overnight. The mixture was quenched with ammonium chloride, was diluted with methylene chloride, was washed successively with dilute sodium bicarbonate, dilute hydrochloric acid and then was dried (potassium carbonate). The solvent was evaporated and the residue was purified by flash chromatography, eluting with 15% ethyl acetate/hexanes, to provide an oil (0.19 g, 69%). This oil was placed in liquid ammonia at −45° C., the mixture was stirred for 8 h and the ammonia was allowed to evaporate overnight at room temperature. The residue was dissolved in methylene chloride (2 mL) at 0° C. under an argon atmosphere and treated with trifluoroacetic acic (0.5 mL). After 45 min, solid sodium bicarbonate was added, the mixture was diluted with methylene chloride, the organic layer was washed with 5% aqueous sodium bicarbonate and then with water. The organic extract was dried (potassium carbonate) and evaporated. The residue was purified by flash chromatography, eluting with 3–20% isopropanol/methylene chloride, to provide a solid: m.p. 53°–55° C.

Analysis Calc. for $C_{16}H_{22}N_4O_2 \cdot 3/4$ $H_2O$: C 60.84, H 7.50, N. 17.74; found: C 60.70, H 7.07, N 17.35.

Example 10

N-[2-(3-Cyclopentyloxy-4-methoxyphenyl)ethyl] acetamide

10a. N-(t-Butoxycarbonyl)-2-(3-cyclopentyloxy-4-methoxyphenyl)ethylamine A solution of 2-(3-cyclopentyloxy-4-methoxyphenyl)ethylamine (2.5 g, 10.6 mmol) in methylene chloride (25 mL) was treated with t-butyloxycarbonylanhydride (2.5 mL, 11 mmol) and stirred under an argon atmosphere for 2 h. The solvent was removed in vacuo and the residue was purified by flash chromatography, during with 1:1 ether/hexanes, to provide a colorless oil.

10b. N-(t-Butoxycarbonyl)-2-(3-cyclopentyloxy-4-methoxyphenyl)-N-methylethylamine A solution of N-(t-butoxycarbonyl)-2-(3-cyclopentyloxy-4-methoxyphenyl) ethylamine (1.2 g, 3.6 mmol) in dimethylformamide (10 mL) was treated with sodium hydride (0.12 g of 80% dispersion, 4 mmol) and stirred at room temperature under an argon atmophere for 2 h. Methyl iodide (0.3 mL, 4.8 mmol) was added and stirring was continued for another 3 h. The solvent was removed in vacuo and the residue was partitioned between methylene chloride and acidic water. The organic layer was dried (potassium carbonate) and evaporated. Purification by flash chromatography, eluting with 3:1 hexanes/ether, provided an oil.

10c. 2-(3-cyclopentyloxy-4-methoxyphenyl)-N-methylethylamine A solution of N-(t-butoxycarbonyl)-2-(3-cyclopentyloxy-4-methoxyphenyl)-N-methylethylamine (0.65 g, 1.86 mmol) in methylene chloride (5 mL) was treated with trifluoroacetic acid (2 mL) and stirred under an argon atmosphere for 1 h. The solvent was removed in vacuo and the residue was partitioned between methylene chloride and 5% sodium bicarbonate. The organic layer was dried (potassium carbonate) and evaporated to an oil.

10 d. N-[2-(3-Cyclopentyloxy-4-methoxyphenyl)ethyl] acetamide A solution of 2-(3-cyclopentyloxy-4-methoxyphenyl)-N-methylethylamine (0.12 g, 0.48 mmol) in pyridine (0.4 mL) and acetic anhydride (0.28 mL) was stirred at room temperature under an argon atmosphere for 24 h. The liquids were evaporated and the residue was purified by flash chromatography, eluting with 97:3 chloroform/methanol, to provide an oil. Analysis Calc. for $C_{17}H_{25}NO_3 \cdot 1/4 H_2O$: C 69.01, H 8.69, N 4.73; found: C 68.81, H 8.70, N 4.58.

Example 11

N-[2-(3-Cyclopentyloxy-4-methoxyphenyl)ethyl]-2-hydroxyacetamide

A solution of 3-cyclopentyloxy-4-methoxyphenethylamine (0.1 g, 0.42 mmol) in tetrahydrofuran (3 mL) was cooled to 0° C. and was treated with triethylamine (0.064 mL, 0.46 mmol) and benzyloxyacetyl chloride (0.066 mL, 0.42 mmol). The reaction was stirred under an argon atmosphere for 0.5 h, then was partitioned between methylene chloride and acidic water. The extract was dried (potassium carbonate) and evaporated. The resulting solid (0.16 g) was dissolved in ethanol, a small amount of 10% palladium on carbon was added, the resulting mixture was hydrogenated at 50 psi for 24 h, then filtered through a pad of Celite and evaporated. Purification by flash chromatography, eluting with 5% methanol/chloroform, provided a solid: m.p. 69.5°–71° C.

Analysis Calc. for $C_{16}H_{23}NO_4 \cdot 1/8 H_2O$: C 65.01, H 7.93, N 4.74; found: C 65.03, H 7.83, N 4.83.

Example 12

N-[2-(3-Cyclopentyloxy-4-methoxyphenyl)ethyl]-2-methoxyacetamide

A solution of 3-cyclopentyloxy-4-methoxyphenethylamine (0.2 g, 0.85 mmol) in tetrahydrofuran (6 mL) was cooled to 0° C. and was treated with triethylamine (0.13 mL, 0.92 mmol) and methoxyacetyl chloride (0.078 mL, 0.85 mmol). The reaction was stirred under an argon atmosphere for 0.25 h, then was partitioned between methylene chloride and water. The extract was dried (potassium carbonate) and evaporated. Purification by flash chromatography, eluting with 5% methanol/chloroform, provided an oil; additional 0.1 g of impure product also obtained).

Analysis Calc. for $C_{17}H_{25}NO_4$: C 66.43, H 8.20, N 4.56; found: C 66.67, H 8.18, N 4.45.

Example 13

N-[2-Cyano-2-(3-cyclopentyloxy-4-methoxyphenyl) ethyl]-2-hydroxyacetamide

13a. α-Bromo-3-cyclopentyloxy-4-methoxytoluene To 3-cyclopentyloxy-4-methoxybenzaldehyde (5.0 g, 22.7 mmol) was added lithium bromide (3.94 g, 45.4 mmol) and acetonitrile (25 mL). Upon dissolution, the reaction mixture was cooled to 0° C. Trimethylsilyl chloride (4.32 mL, 34.0 mmol) was slowly added and the reaction mixture was allowed to warm to room temperature and stirred for 15 min. The reaction mixture was again cooled to 0° C. and 1,1,3,3-tetramethyldisiloxane (6.68 mL, 34.0 mmol) was added dropwise. The resulting mixture was allowed to warm to room temperature. After stirring for 2 h, the mixture was separated into two layers. The lower layer was removed, diluted with methylene chloride and filtered. The filtrate was concentrated under reduced pressure, dissolved in methylene chloride and filtered. The solvent was removed in vacuo to provide a light tan oil, which was used without further purification.

13b. (3-Cyclopentyloxy-4-methoxyphenyl)acetonitrile To a solution of α-bromo-3-cyclopentyloxy-4-methoxytoluene (6.6 g, 23.0 mmol) in dimethylformamide (10 mL) under an argon atmosphere was added a suspension of powdered sodium cyanide (2.5 g, 51.0 mmol) in dimethylformamide (40 mL). The resulting mixture was stirred at room temperature for 24 h, then poured into cold water (250 mL) and extracted three times with ether/ethyl acetate. The combined organic extracts were washed three times with water and dried (sodium sulfate). The solvent was removed in vacuo and the residue was purified by flash chromatography, eluting with 30% ethyl acetate/hexanes, to provide a pale yellow oil.

13c. Methyl 2-cyano-2-(3-cyclopentyloxy-4-methoxyphenyl)acetate. To a suspension of sodium hydride (0.69 g of an 80% suspension in mineral oil washed three times with pentane, 22.44 mmol) in toluene (25 mL) under an argon atmosphere was added a solution of freshly distilled dimethyl carbonate (1.30 mL, 15.1 mmol) and (3-cyclopentyloxy-4-methoxyphenyl)acetonitrile (1.71 g, 7.44 mmol) in toluene (5 mL). The resulting mixture was heated at reflux for 1.25 h, with most of the solvent then removed by distillation, and the remainder was stirred overnight at room temperature. The mixture was cooled to 0° C., partitioned between ice water and ether, and acidified. The product was extracted with ether, the extract was dried (sodium sulfate) and the solvent was removed in vacuo to provide an oil.

13d. 2-Cyano-2-(3-cyclopentyloxy-4-methoxyphenyl) acetamide A solution of methyl 2-cyano-2-(3-cyclopentyloxy-4-methoxyphenyl)acetate (2.1 g, 7.26 mmol) in concentrated ammonium hydroxide (50 mL) was stirred at room temperature for four days. A thick white precipitate formed after the first half hour. The reaction was cooled to 0° C., acidified to pH 2–3 with 10% aqueous hydrochloric acid, extracted three times with methylene chloride/methanol and dried (magnesium sulfate). The solvent was removed in vacuo to provide an off-white solid: m.p. 160°–162° C.

13e. 3-(t-Butoxycarbonylamino)-2-(3-cyclopentyloxy-4-methoxyphenyl)propioamide

To a solution of 2-cyano-2-(3-cyclopentyloxy-4-methoxyphenyl)acetamide (0.504 g, 1.85 mmol) in methanol (25 mL) was added 70% perchloric acid (0.18 mL, 1.9 mmol) and 10% palladium on carbon (0.03 g). The resulting mixture was hydrogenated at 50 psi for 2 h and filtered through a pad of Celite. The filtrate was concentrated in vacuo. The solid residue was partitioned between methylene chloride and aqueous sodium carbonate and the organic layer was dried (sodium sulfate). The solvent was removed in vacuo, and the residue was dissolved in methylene chloride (25 mL) and treated with di-t-butyldicarbonate (0.5 mL, 2.18 mmol). After 20 h, the solvent was evaporated and the residue was purified by flash chromatography, eluting with 1:1 ethyl acetate/hexanes, to provide a pale yellow solid.

13f. 3-(t-Butoxycarbonylamino)-2-(3-cyclopentyloxy-4-methoxyphenyl)propionitrile A solution of 3-(t-butoxycarbonylamino)-2-(3-cyclopentyloxy-4-methoxyphenyl)propioamide (0.29 g, 0.75 mmol) in dry tetrahydrofuran (5 mL) was treated with pyridine (0.135 mL, 1.66 mmol) and with trifluoroacetic anhydride (0.12 mL, 0.83 mmol) dropwise. The reaction was stirred at room temperature for 1.5 h, then quenched with ice and partitioned between methylene chloride and water. The organic extract was dried (magnesium sulfate) and concentrated. Purification by flash chromatography, eluting with 3:7 ethyl acetate/hexanes, provided an orange-yellow oil.

13g. 3-Amino-2-(3-cyclopentyloxy-4-methoxyphenyl) propionitrile A solution of 3-(t-butoxycarbonylamino)-2-(3-cyclopentyloxy-4-methoxyphenyl)propionitrile (0.26 g, 0.71 mmol) in methylene chloride (5 mL) cooled to 0° C. was treated with the dropwise addition of trifluoroacetic acid (1.0 mL) and stirred under argon for 2 h at 0° C. and 2 h at room temperature. The reaction was neutralized with solid sodium bicarbonate, diluted with methylene chloride and washed with aqueous sodium bicarbonate and then with water. The organic extract was dried (potassium carbonate) and evaporated to provide a yellow oil.

13 h. N-[2-Cyano-2-(3-cyclopentyloxy-4methoxyphenyl) ethyl]-2-acetoxyacetamide A solution of 3-amino-2-(3-cyclopentyloxy-4-methoxyphenyl)propionitrile (0.095 g, 0.36 mmol) in methylene chloride (2 mL) was cooled to 0° C. and was treated with triethylamine (0.057 mL, 0.43 mmol) and acetoacetyl chloride (0.045 mL, 0.4 mmol). The reaction was stirred under an argon atmosphere for 1.5 h, then was treated with aqueous ammonium chloride and was extracted three times with methylene chloride. The extract was dried (magnesium sulfate) and evaporated. Purification by flash chromatography, eluting with 1:4 ethyl acetate/ methylene chloride, provided a colorless oil.

13i. N-[2-Cyano-2-(3-cyclopentyloxy-4-methoxyphenyl) ethyl]-2-hydroxyacetamide A solution of N-[2-cyano-2-(3-cyclopentyloxy-4-methoxyphenyl)ethyl]-2-acetoxyacetamide (0.102 g, 0.28 mmol) in methanol (5 mL) was treated with powdered potassium carbonate (0.096 g, 0.69 mmol) and stirred for 15 min. The mixture was diluted with water, was extracted three times with methylene chloride and the organic extract was dried (potassium carbonate) and evaporated. Purification by flash chromatography, eluting with 3% methanol/methylene chloride, provided an oil.

Analysis Calc. for $C_{17}H_{22}N_2O_4 \cdot 1/4\ H_2O$: C 63.24, H 7.02, N 8.68; found: C 63.44, H 6.85, N 8.52.

Example 14

N-[2-Cyano-2-(3-cyclopentyloxy-4-methoxyphenyl) ethyl]urea

To a solution of 2-cyano-2-(3-cyclopentyloxy-4-methoxyphenyl)ethylamine [3-amino-2-(3-cyclopentyloxy-4-methoxyphenyl)propionitrile, 0.17 g, 0.66 mmol] in tetrahydrofuran (5 mL) under an argon atmosphere was added trimethylsilyl isocyanate (0.13 mL, 0.96 mmol). The resulting mixture was stirred overnight at room temperature. Aqueous ammonium chloride was added, the mixture was extracted three times with 5% methanol/methylene chloride, the extract was dried (potassium carbonate) and evaporated. Purification of the residue by flash chromatography, eluting with 4% methanol/methylene chloride, provided the urea as a white solid: m.p. 55°–61° C. (sublimes).

Analysis Calc. for $C_{16}H_{21}N_3O_3 \cdot 1/4H_2O$: C 62.42, H 7.03, N 13.65; found: C 62.35, H 6.75, N 13.54.

Example 15

N-[2-(3-Cyclopentyloxy-4-methoxyphenyl)ethyl]-2-aminoacetamide

15a. N-[2-(3-Cyclopentyloxy-4-methoxyphenyl)ethyl]-2-t-butyloxycarbonylaminoacetamide A solution of 3-cyclopentyloxy-4-methoxyphenethylamine (0.32 g, 1.37 mmol) in methylene chloride (5 mL) at room temperature under an argon atmosphere was treated with triethylamine (0.19 mL, 1.37 mmol), N,N-dimethylaminopyridine (0.17 g, 1.37 mmol) and N-t-butyloxycarbonylglycine-N-hydroxysuccinimide ester (0.37 g, 1.37 mmol). The reaction was stirred for 2.5 h, then was partitioned between methylene chloride and acidic water and extracted twice. The extract was dried (potassium carbonate) and evaporated. The crude product was combined with that of a similar reaction conducted on the phenethylamine (0.03 g, 0.13 mmol) and was purified by flash chromatography, eluting with 5% methanol/chloroform, to provide an oil.

Analysis Calc. for $C_{21}H_{32}N_2O_5 \cdot 1/4\ H_2O$: C 63.53, H 8.25, N 7.06; found: C 63.43, H 7.89, N 7.06.

15b. N-[2-(3-cyclopentyloxy-4-methoxyphenyl)ethyl]-2-aminoacetamide A solution of N-[2-(3-cyclopentyloxy-4-methoxyphenyl)ethyl]-2-t-butyloxycarbonylaminoacetamide (0.53 g, 1.35 mmol) in methylene chloride (16 mL) cooled to 0° C. was treated with the dropwise addition of trifluoroacetic acid (1.7 mL), was allowed to come to room temperature and was stirred for 2.5 h. The liquids were evaporated, the residue was partitioned between methylene chloride and saturated aqueous sodium bicarbonate and was extracted three times. The organic extract was dried (potassium carbonate) and evaporated. Purification by flash chromatography, eluting with 5% methanol/chloroform, provided a solid: m.p. 57°–60° C.

Analysis Calc. for $C_{16}H_{24}N_2O_3$: C 65.73, H 8.27, N 9.58; found: C 65.39, H 8.27, N 9.18.

Example 16

(4R)-N-[2-(3-Cyclopentyloxy-4-methoxyphenyl) ethyl]-2,2-dimethyl- 1,3-dioxolane-4-carboxamide 16a. (4R)-2.2-dimethyl-1,3-dioxolane-4-carboxylic acid To a solution of methyl (4R)-2,2-dimethyl-1,3-dioxolane-4-carboxylate (2.21 g, 13.7 mmol) in methanol (60 mL) under an argon atmosphere was added lithium hydroxide monohydrate (0.61 g, 14.5 mmol). After stirring at room temperature for 3 h, the reaction mixture was concentrated under reduced pressure. The residue was acidified with 10% HCl and extracted with methylene chloride. The organic extract was washed with water and dried (magnesium sulfate). The solvent was removed in vacuo to provide the acid, which was used without further purification.

16b. (4R)-N-[2-(3-Cyclopentyloxy-4-methoxyphenyl) ethyl]-2,2-dimethyl-1,3-dioxolane-4-carboxamide To a solution of (4R)-2,2-dimethyl-1,3-dioxolane-4-carboxylic acid (0.50 g, 3.42 mmol) in 1,2-dimethoxyethane (10 mL) under an argon atmosphere was added N-methylmorpholine (0.44 mL, 3.93 mmol) and ethyl chloroformate (0.38 mL, 3.93 mmol). The resulting mixture was stirred at room temperature for 4 h, at which time was added a solution of 2-(3-cyclopentyloxy-4-methoxyphenyl)ethylamine (0.75 g, 3.19 mmol) in 1,2-dimethoxyethane (5 mL). After stirring for 2 h at room temperature, the mixture was concentrated under reduced pressure. The residue was dissolved in methylene chloride and washed successively with 10% HCl (twice), aqueous sodium bicarbonate and water and dried (potassium carbonate). The solvent was removed in vacuo and the residue was purified by flash chromatography, eluting with 35% ethyl acetate/hexanes, to provide the carboxamide as a pale yellow oil.

Analysis Calc. for $C_{20}H_{29}NO_5 \cdot 1/2\ H_2O$: C 64.50, H 8.12, N 3.76; found: C 64.68, H 7.84, N 3.86.

Example 17

(2R)-N-[2-(3-Cyclopentyloxy-4-methoxyphenyl) ethyl]-2,3-dihydroxypropanamide

To a solution of (4R)-N-[2-(3-cyclopentyloxy-4-methoxyphenyl)ethyl]-2,2-dimethyl-1,3-dioxolane-4-carboxamide (0.48 g, 1.32 mmol) in tetrahydrofuran (2.5 mL) under an argon atmosphere was added hydrochloric acid (1M, 2.5 mL) and the resulting mixture was stirred at room temperature for 5 h. Potassium carbonate was added, and the mixture was partitioned between methylene chloride and water. The organic extract was washed with saturated aqueous sodium chloride and dried (potassium carbonate). Removal of the solvent in vacuo and purification of the residue by flash chromatography, eluting with 5% methanol/methylene chloride, provided a solid (0.36 g, 85%): m.p. 58°–59° C.

Analysis Calc. for $C_{17}H_{25}NO_5 \cdot 1/10\ H_2O$: C 62.79, H 7.81, N 4.31; found: C 62.63, H 7.81, N 4.71.

Example 18

(2S)-N-[2-(3-Cyclopentyloxy-4-methoxyphenyl) ethyl]-2,3-dihydroxypropanamide and Isobutyl N-[2-(3-cyclopentyloxy-4-methoxyphenyl)ethyl] carbamate 18a. (4S)-2,2-Dimethyl-1,3-dioxolane-4-carboxylic acid. To a solution of methyl (4S)-2,2-dimethyl-1,3-dioxolane-4-carboxylate (0.55 g, 3.43 mmol) in methanol (15 mL) under an argon atmosphere was added lithium hydroxide monohydrate (0.15 g, 3.64 mmol). After stirring at room temperature for 2.5 h, the reaction mixture was concentrated under reduced pressure. The residue was acidified with 10% HCl and extracted with methylene chloride. The organic extract was washed with water and dried (magnesium sulfate). The solvent was removed in vacuo to provide a colorless oil, which was used without further purification.

18b. (2S)-N-[2-(3-Cyclopentyloxy-4-methoxyphenyl) ethyl]-2,3-dihydroxypropanamide and Isobutyl N-[2-(3-cyclopentyloxy-4-methoxyphenyl)ethyl]carbamate. To a solution of (4S)-2,2-dimethyl-1,3-dioxolane-4-carboxylic acid (0.46 g, 3.19 mmol) in 1,2-dimethoxyethane (10 mL) under an argon atmosphere was added N-methylmorpholine (0.41 mL, 3.67 mmol) and isobutyl chloroformate (0.48 mL, 3.67 mmol). The resulting mixture was stirred at room temperature for 1 h, at which time was added a solution of 2-(3-cyclopentyloxy-4-methoxyphenyl)ethylamine (0.75 g, 3.19 mmol) in 1,2-dimethoxyethane (5 mL). After stirring for 6 h at room temperature, the mixture was concentrated under reduced pressure. The residue was dissolved in methylene chloride and washed successively with 10% HCl, aqueous sodium bicarbonate and water and dried (potassium carbonate). The solvent was removed in vacuo and the residue was purified by flash chromatography, eluting with 3% methanol/methylene chloride to provide (2S)-N-[2-(3-cyclopentyloxy-4-methoxyphenyl)ethyl]-2,3-dihydroxypropanamide: m.p. 57°–58.5° C.

Analysis Calc. for $C_{17}H_{25}NO_5$: C 63.14, H 7.79, N 4.33; found: C 62.72, H 7.60, N 4.28.

Also isolated was isobutyl N-[2-(3-cyclopentyloxy-4-methoxyphenyl)ethyl]carbamate as a white solid: m.p. 54°–55° C.

Analysis Calc. for $C_{19}H_{29}NO_4$: C 68.03, H 8.71, N 4.18; found: C 67.95, H 8.70, N 4.15.

Example 19

Formulations for pharmaceutical use incorporating compounds of the present invention can be prepared in various forms and with numerous excipients. Examples of such formulations are given below.

Inhalant Formulation

A compound of formula I, (1 µg to 100 mg) is aerosolized from a metered dose inhaler to deliver the desired mount of drug per use.

|   | Tablets/Ingredients | Per Tablet |
|---|---|---|
| 1. | Active ingredient (compound of formula. I) | 40 mg |
| 2. | Corn Starch | 20 mg |
| 3. | Alginic acid | 20 mg |
| 4. | Sodium alginate | 20 mg |
| 5. | Mg stearate | 1.3 mg |
|   |   | 01.3 mg |

Procedure for Tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is convened to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount f a compound of formula I in polyethylene glycol with heating. This solution is then diluted with water for injections Ph Eur. (to 100 ml). The solution is then sterilized by filtration through a 0.22 micron membrane filter and sealed in sterile containers.

What is claimed is:

1. A compound of formula I

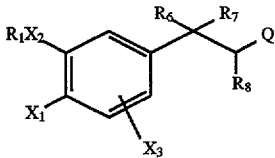

or a salt thereof, where Q is a radical of formula

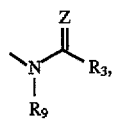

$R_1$ is $C_{7-11}$ polycycloalkyl, $C_{3-6}$ cycloalkyl wherein the cycloalkyl moieties are unsubstituted or substituted by 1 to 3 methyl groups or one ethyl group;

$R_2$ is —$CH_3$ or —$CH_2CH_3$ unsubstituted or substituted by 1 or more halogens:

$R_3$ is lower alkyl unsubstituted or substituted by one or more halogens, —$CR_4R_5OR_4$ or —$CR_4(OR_4)CR_4R_5OR_4$;

$R_4$ and $R_5$ are independently hydrogen, methyl or ethyl;

$R_6$ is hydrogen, halogen, —$C_{1-4}$ alkyl, halo-substituted $C_{1-4}$ alkyl, —CH=$CR_4R_5$, cyclopropyl unsubstituted or substituted by $R_4$, or —C≡$CR_4$;

$R_7$ is hydrogen, F, or —$CH_3$ unsubstituted or substituted by 1 to 3 fluoro groups;

$R_8$ is H, F, or $C_{1-2}$ alkyl optionally substituted by 1 or more fluoro groups;

$R_9$ is H or unsubstituted or substituted $C_{1-6}$ alkyl, wherein optional substituents are from one to three groups independently selected from the group consisting of —$CH_3$ or —$CH_2CH_3$ unsubstituted or substituted by 1 or more halogens;

$X_1$ is $YR_2$, $X_2$ is O;

$X_3$ is hydrogen, halogen or $X_1$;

Y is O, S, SO or $SO_2$;

Z is O.

2. A composition of matter comprising a compound of formula I according to claim 1 in admixture with an excipient.

3. A method for treating allergic and inflammatory diseases which comprises administering to a mammal in need thereof an effective amount of a compound of Formula I either alone or in admixture with a pharmaceutically acceptable excipient.

* * * * *